(12) United States Patent
Reimels et al.

(10) Patent No.: US 9,642,654 B2
(45) Date of Patent: May 9, 2017

(54) SINGLE ACTION LOCKING PEDICLE SCREWDRIVER

(71) Applicant: Alphatec Spine, Inc., Carlsbad, CA (US)

(72) Inventors: William Reimels, Oceanside, CA (US); Tara Stevenson, La Jolla, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 336 days.

(21) Appl. No.: 14/305,254

(22) Filed: Jun. 16, 2014

(65) Prior Publication Data

US 2015/0359572 A1 Dec. 17, 2015

(51) Int. Cl.
*A61B 17/58* (2006.01)
*A61B 17/70* (2006.01)

(52) U.S. Cl.
CPC ...... *A61B 17/7082* (2013.01); *A61B 17/7032* (2013.01)

(58) Field of Classification Search
CPC ............ A61B 17/7082; A61B 17/7076; A61B 17/7077; A61B 17/708
USPC ........................................................ 606/104
See application file for complete search history.

(56) References Cited

U.S. PATENT DOCUMENTS

| | | | |
|---|---|---|---|
| 6,189,422 B1 * | 2/2001 | Stihl | A61B 17/8891 606/104 |
| 7,887,539 B2 * | 2/2011 | Dunbar, Jr. | A61B 17/7091 606/104 |
| 8,231,635 B2 | 7/2012 | Sharifi-Mehr et al. | |
| 8,394,108 B2 * | 3/2013 | McLean | A61B 17/7082 606/104 |
| 2007/0270880 A1 * | 11/2007 | Lindemann | A61B 17/8888 606/104 |
| 2008/0221583 A1 | 9/2008 | Sharifi-Mehr et al. | |
| 2008/0243133 A1 * | 10/2008 | Heinz | B25B 23/101 606/104 |
| 2009/0326545 A1 * | 12/2009 | Schaffhausen | A61B 17/8891 606/104 |
| 2012/0253355 A1 * | 10/2012 | Murray | A61B 17/8888 606/104 |
| 2013/0282019 A1 * | 10/2013 | Bouliane | A61B 17/7082 606/104 |
| 2015/0257797 A1 * | 9/2015 | Biedermann | A61B 17/7001 606/305 |
| 2016/0038182 A1 * | 2/2016 | Gorek | A61B 1/32 606/86 A |

\* cited by examiner

*Primary Examiner* — Matthew Lawson
(74) *Attorney, Agent, or Firm* — Dinsmore & Shohl LLP (57) ABSTRACT

An instrument for attaching a driver shaft to a screw assembly using a thrusting motion. The instrument has a main shaft, a locking tube, and a driver shaft. The locking tube is slidably mounted within the main shaft and the driver shaft is slidably mounted within the locking tube. The locking tube is configured to urge a jaw assembly of the instrument into a tensioned engagement with a body member of the screw assembly. A locking mechanism is also included and is configured to lock the driver shaft in a fixed position relative to the locking tube. The locking mechanism may be configured to lock the driver shaft with respect to the locking tube after a distal end of the main shaft engages the screw assembly using the single action.

19 Claims, 7 Drawing Sheets

SINGLE ACTION LOCKING PEDICLE SCREWDRIVER

FIELD OF THE INVENTION

The present invention is related to a medical instrument and in particular to a medical instrument for attaching a driver shaft to a screw assembly using a single action.

BACKGROUND OF THE INVENTION

Instruments for screwing or driving screws into bone material are known. The screws are typically presented to the surgeon in a tray, wherein the heads of the screw are exposed. To maintain a sterile environment, the heads of the screw are configured to engage the instrument. Accordingly, the surgeon stabs the head of the screw with an end of the instrument to engage the screw head in a temporary setting, and then must secure the head to the instrument. Current instruments require two hands to perform such an act. One hand is used to engage the head in a temporary setting. However a second hand is needed to secure the head of the screw to the instrument. Specifically, one hand supports the driver while the other hand rotates a sleeve in a labor intensive action to threadedly engage the screw head to the end of the instrument. Accordingly it remains desirable to have an instrument which requires the use of a single hand to engage the head of a screw. It further remains desirable to have an instrument which engages the head of the screw in a single motion.

SUMMARY OF THE INVENTION

An instrument for attaching a driver shaft to a screw assembly using a single action, e.g. a one-push motion is provided. The instrument has a main shaft, a locking tube, and a driver shaft. The locking tube is slidably mounted within the main shaft and the driver shaft is slidably mounted within the locking tube. The locking tube is configured to urge an end portion of the instrument into a tensioned engagement with an inner surface of the head of the screw. A locking mechanism is also included and is configured to lock the locking tube and/or the driver shaft in a fixed position relative to the main shaft when the main shaft is translated distally. The locking mechanism is further configured to be actuated upon a distal advancement of the main shaft. The locking mechanism may be configured to lock the driver shaft with respect to the locking tube and the main shaft after a distal end of the main shaft engages the screw assembly using the single action.

The instrument may also include a housing having a cover and a release knob. The housing is configured to be gripped by a user, and store the locking mechanism. The main shaft has a proximal end that is coupled to the housing and a distal end with a screw jaw assembly for selectively attaching to the screw assembly. The locking tube within the main shaft has a proximal end that is coupled to the housing and a distal end that is proximate the screw jaw assembly for lockingly engaging jaws of the screw jaw assembly with the screw assembly. The driver shaft within the locking tube also has a proximal end that extends through the housing and a distal end that extends through the screw assembly jaw for engaging and driving a screw of the screw assembly.

The screw jaw assembly has a pair of oppositely disposed jaws and each of the jaws has a contoured edge that is dimensioned to engage a portion of a body member of the screw assembly. In addition, the contoured edge of each jaw can be complementary in shape with an edge of a jaw slot or landing that is part of the body member.

The distal end of the locking tube slides between and applies a force to the pair of oppositely disposed jaws in an outwardly direction during the single action. In addition, the force pushes the contoured edge of each of the pair of jaws against the jaw slot edge on the body member and thereby lockingly engages the screw jaw assembly and the main shaft to the screw assembly.

The locking tube can include the locking mechanism mentioned above in the form of a driver shaft lock that is operable to lockingly engage the driver shaft in a fixed position relative to the locking tube by translating the distal movement of the main shaft. Specifically, the driver shaft is locked with respect to the locking tube and/or the main shaft when the main shaft is advanced distally to a predetermined location on the driver shaft. Accordingly, the head of the screw is fixed to the end of the instrument, and the driver shaft is fixed with respect to the main shaft and the locking tube in a single action.

In an illustrative example, the driver shaft lock can be a pair of locking plates that bind against the driver shaft when the distal movement of the main shaft pivots a pair of opposing edges of the locking plates into a binding engagement of the driver shaft. In another illustrative example of a drive shaft lock, the driver shaft lock can be a spring loaded detent, a pin and groove catch, and the like. In is appreciated that the distal end of the driver shaft is engaged with a head of the screw when the driver shaft lock lockingly engages the driver shaft.

The instrument can also include a screw jaw assembly tensioner that is operable to pull on the screw jaw assembly in a direction towards the housing and away from the distal end of the driver shaft. The pull or force on the screw jaw assembly in the direction towards the housing ensures that the driver shaft is in tight engagement with the head of the screw and thereby removes any slack between the instrument and the screw assembly. In this manner a desirable tactile feel is provided to a surgeon that is holding the instrument and screwing a screw into a surgical site.

BRIEF DESCRIPTION OF THE DRAWINGS

A better understanding of the present invention will be had upon reference to the following detailed description when read in conjunction with the accompanying drawings wherein like reference characters refer to like parts throughout the several views and in which.

DETAILED DESCRIPTION OF THE INVENTION

An instrument 10 that simplifies secure attachment of a screw assembly using a single-action locking mechanism 500 actuated by a distal advancement of the instrument 10 is provided. As such, attachment, locking and alignment of a screw assembly 400 to the instrument 10 is accomplished by simply thrusting the end of the instrument 10 into the head 404 of the screw assembly 400 and wherein the thrust not only locks the instrument to the screw assembly, but may also generate a preload condition within the screw assembly 400.

Figure 1:
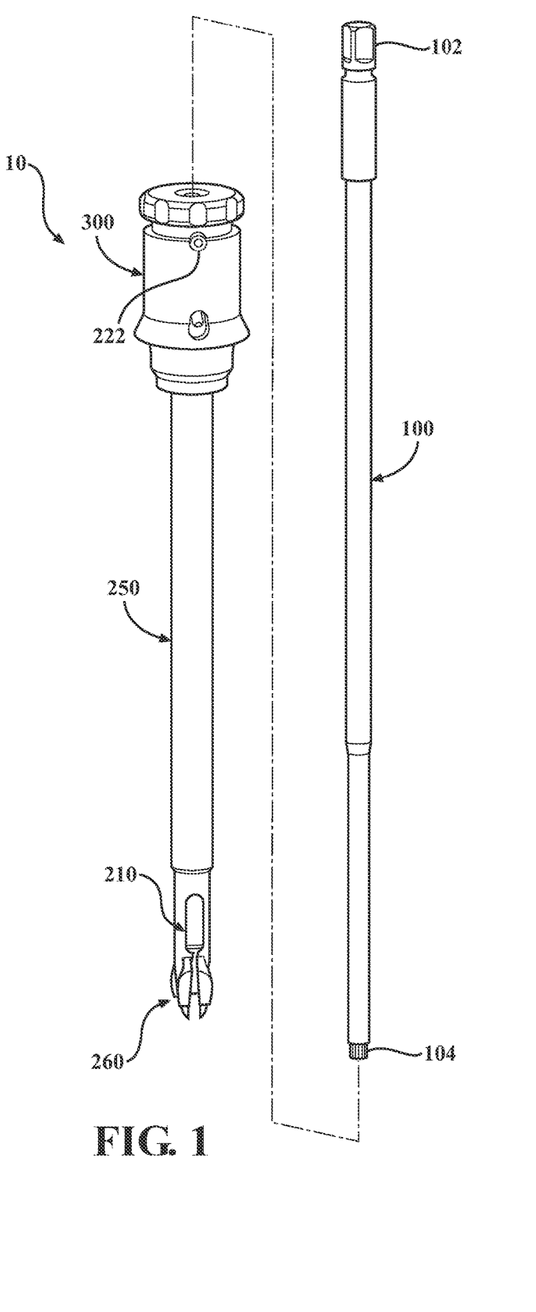
FIG. 1 is a perspective view of an illustrative embodiment of the invention.

Turning now to FIG. 1, an embodiment of the instrument 10 is shown at reference numeral 10. The instrument 10 has a main shaft 250 having a locking tube 210, a housing 300, and a driver shaft 100. The driver shaft 100 has a distal end 104 opposite a proximal end 102. In addition, a handle known to those skilled in the art (not shown) can be attached to the proximal end 102 in order to assist a surgeon rotating the driver shaft 100. The main shaft 250 is a generally tubular structure having open ends. The main shaft 250 includes a screw jaw assembly 260. Housing 300 is connected to the locking tube 210 by means of cam screws 222.

Preferably, the driver shaft 100 is formed of a solid, durable and rigid material accepted for medical use. The locking tube 210 is also of a tubular dimension, having an outer diameter less than an inner diameter of the main shaft 250 and more than a diameter of the driver shaft 100. The driver shaft 100 and the locking tube 210 are slidably mounted within the main shaft 250, a portion of the driver shaft 100 is slidably mounted within the locking tube 210.

The instrument 10 further includes a locking mechanism 500 configured to activate and lock the locking tube 210 to the driver shaft 100 with respect to the main shaft 250 when the locking tube is translated between the jaw assembly 260 by sliding the housing 300 distal towards the jaw assembly 260. When the driver shaft 100 is locked, the locking tube 210 is operable to pull on the screw jaw assembly 260 in a direction towards the housing 300 and away from the distal end of the driver shaft 104. Preferably, the pull or force on the screw jaw assembly 260 in the direction towards the housing 300 ensures that the driver shaft 100 is in tight engagement with the head of a screw 404 (see FIG. 4) and thereby removes any slack between the instrument 10 and the screw assembly 400 to allow the transmission of tactile feedback of a screw being screwed into a patient.

Figure 2:
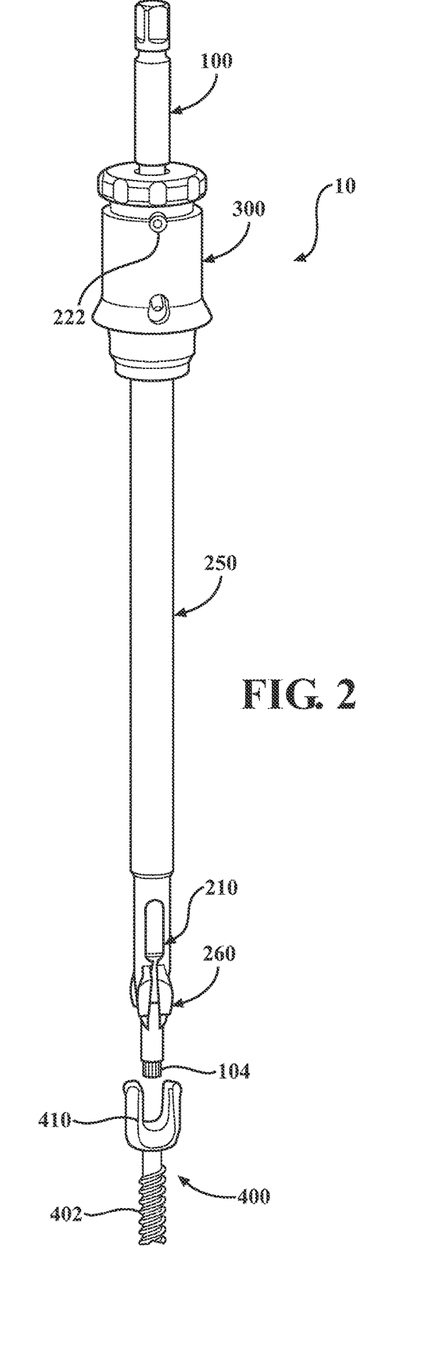
FIG. 2 is a perspective view of the instrument shown in FIG. 1 fully assembled.

FIG. 2 illustrates the instrument 10 with the driver shaft 100 slidably mounted within the main shaft 250 and the distal end 104 extending past or through the jaw assembly 260. Also shown in FIG. 2 is a screw assembly 400 that contains a screw 402 and a body member 410, all of which to be discussed in greater detail below. The force applied by the instrument 10 aligns the screw 402 and body member 410 with the driver shaft 100.

Figure 3:
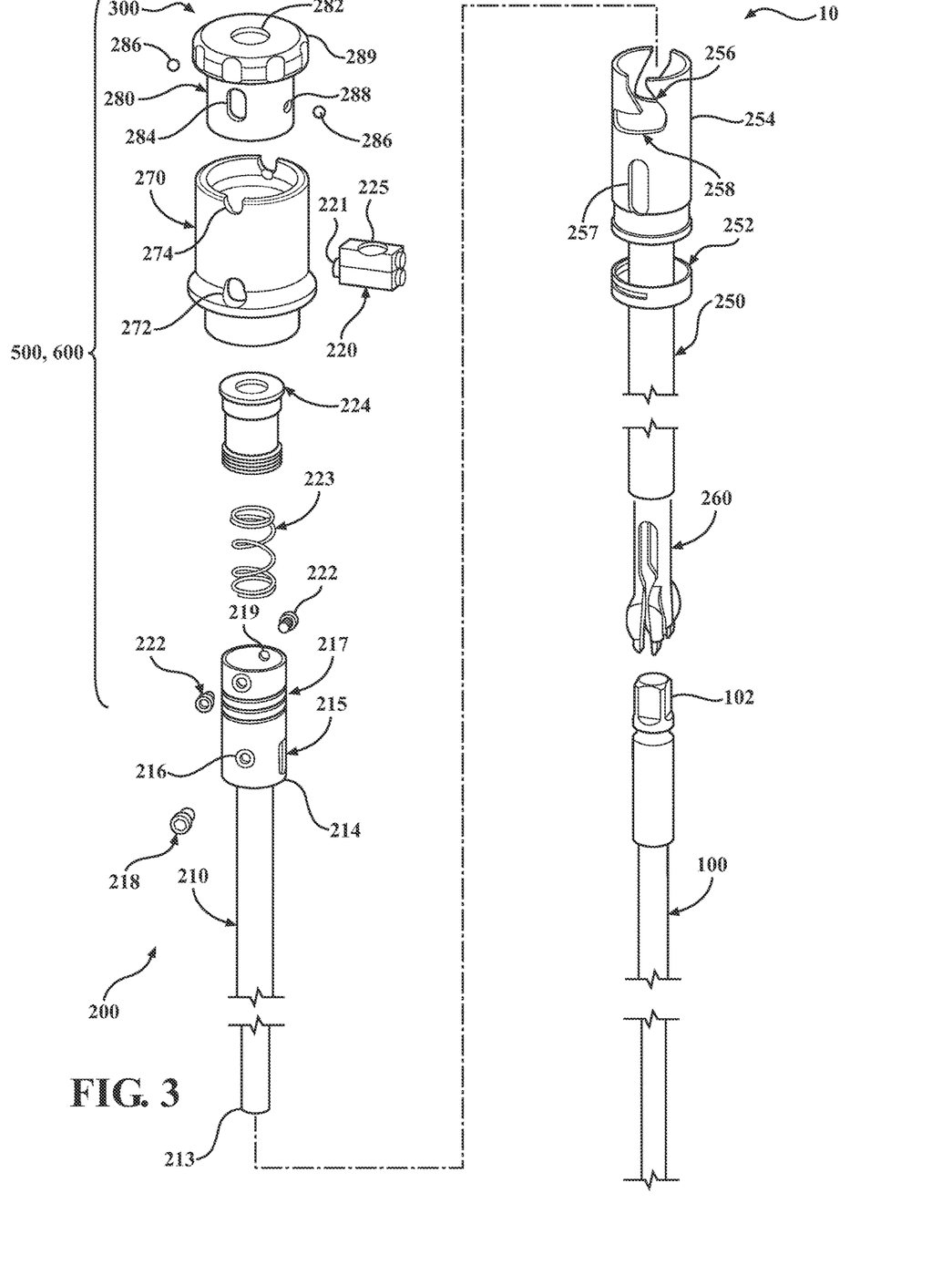
FIG. 3 is an exploded perspective view of the instrument shown in FIG. 1.
Figure 4:
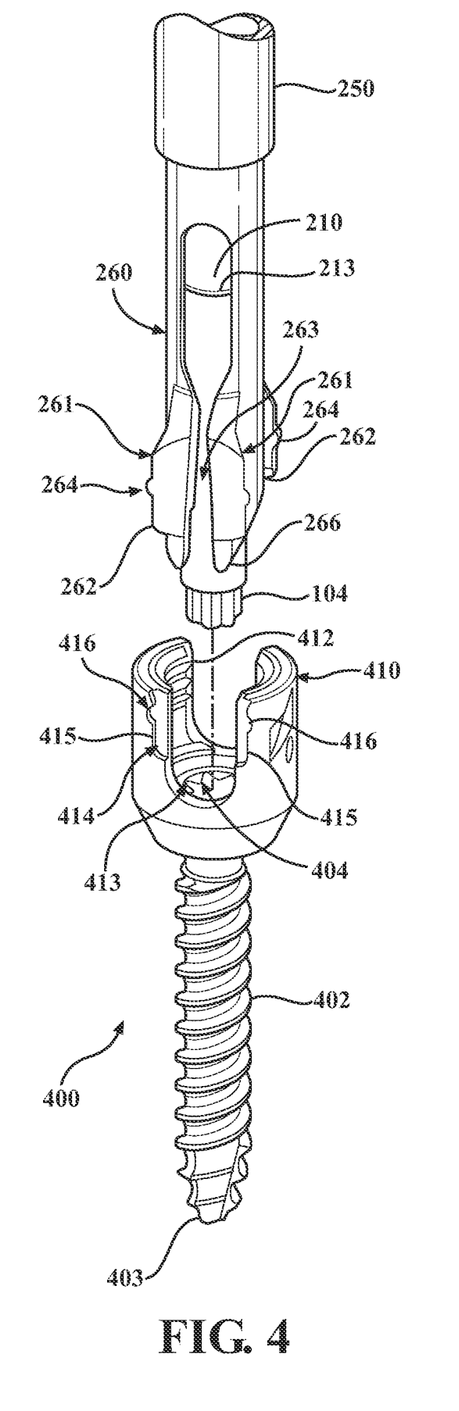
FIG. 4 is a perspective view of a distal end of the instrument shown in FIG. 1 before being attached to a screw assembly.

FIGS. 3 and 4 provide an exploded view of the instrument 10, particularly the housing 300 and locking mechanism 500. As shown in FIG. 3, a proximal end of the main shaft 250 has a locking plate spring clip 252 and an inner housing 254 with a cam raceway 256, a cam locking ramp 258 and a housing cover screw slot 257. In addition to the proximal end of the main shaft 250, a locking tube 210 which is dimensioned to be slidably mounted within the proximal end is shown. The locking tube 210 includes a distal end 213 and a locking tube housing 214. The locking tube housing 214 has a housing cover screw aperture 216 which affords for a housing cover screw 218 to be threadably engaged. In the alternative to the locking plate spring clip 252 being part of the main shaft 250, the locking tube housing 214 can include the locking plate spring clip 252.

The locking tube housing 214 may further include a locking plate pivot slot 215, a cam torsion spring 217 and a pair of apertures 219. Locking plates 220 with a post 221 can be included, as well as a pair of cam screws 222. It is appreciated that the post 221 can be located off-center with respect to a width of the locking plates 220. In addition, the off-center location of the post 221 affords for tilting of the plates 220 when the post 221 contacts the locking plate spring clip 252 as discussed below. A locking plate spring 223 keeps the locking plates from tilting and allows free passage of the driver shaft 100. The locking plate spring 223 is dimensioned to fit within the housing 214 and engage with a spring end cap 224 are also shown. Dimensioned to cover or fit outside of the main shaft inner housing 254 is a housing cover 270. The housing cover 270 has a pair of housing cover screw apertures 272 as well as a pair of coupling ball indentations 274.

A release knob 280 is also shown, the release knob 280 having a driver shaft aperture 282, a pair of cam screw slots 284, ball bearings 286, and ball bearing seat surfaces 288. It is appreciated that the release knob 280 can have a ribbed flange 289 that affords for turning of the release knob by a surgeon or assistant's hand. As shown by FIGS. 1-4, the driver shaft 100 and the locking tube 210 fit within the main shaft 250. In addition, assembly of the main shaft inner housing 254, locking tube housing 214, housing cover 270, release knob 280 and the various components associated therewith and described above, makeup or constitute the housing 300 and affords for the single action motion described above and discussed in greater detail below.

With regards to engagement of the screw jaw assembly 260 of the instrument 10 with the screw assembly 400, FIG. 4 provides an enlarged view of the distal end of the instrument 10 just before and proximate to being attached to the screw assembly 400. As shown in the figure, the jaw assembly 260 has a pair of oppositely disposed jaws 261 with a slit 263 therebetween. In addition, the jaws 261 are flexible in that they can be moved towards each other and away from each other due to the design/slit 263. Each of the jaws 261 has a jaw tip 266 and an outer edge 262 with an outwardly extending projection 264.

The screw assembly 400 has a threaded screw 402 with a tip 403 and a female screw head 404. It is appreciated that the female screw head or screw socket 404 is complementary with the distal end 104 of the driver shaft 100 as is known to those skilled in the art. In addition, the screw assembly 400 has a body member 410 that is movably mounted to the screw 402 via the screw head 404. In some instances, the screw head 404 has a spherical shape and the body member 410 has spherical shaped socket that is complimentary in size to the spherical shaped screw head 404. The body member 410 can have internal threads 412 that are used to threadingly engage a setscrew for retaining a fixation rod within a channel 413 of the body member 410 as is known to those skilled in the art. The body member 410 also has a slot or landing 414 that has an outer edge 415 with an indentation 416. It is appreciated that the outer edge 415 is complementary with the outer edge 262 of the jaw 261 and thus the projection 264 of the jaw 261 fits within and is complementary with the indentation 416 of the landing 414.

Figure 5:
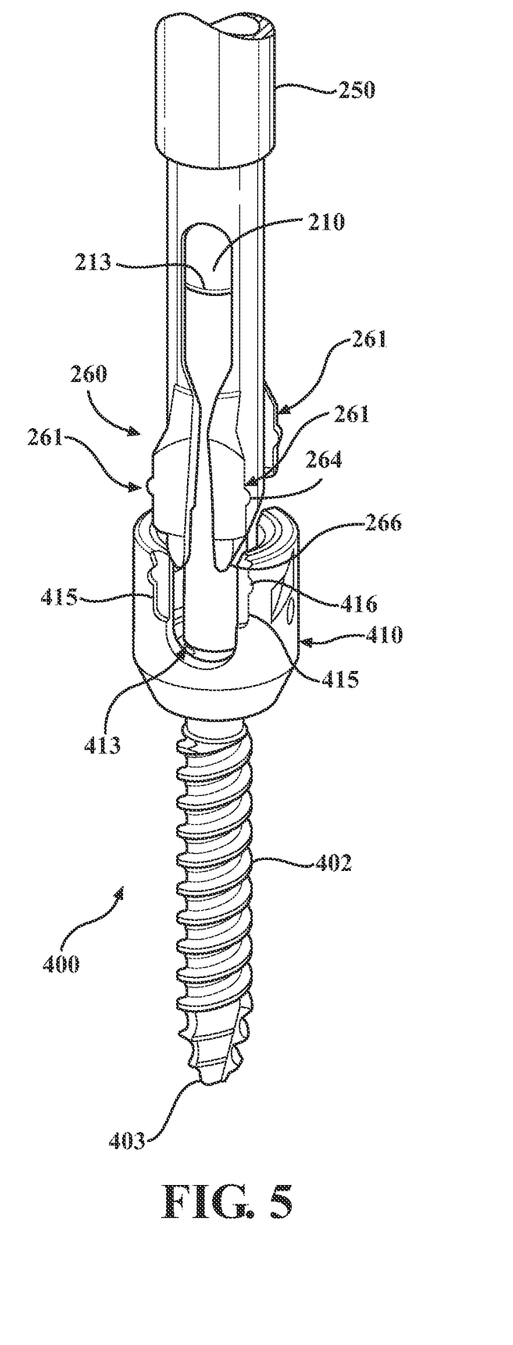
FIG. 5 is a perspective view of a distal end of the instrument shown in FIG. 1 while being attached to a screw assembly.

Turning now to FIG. 5, a schematic illustration of the instrument 10 being inserted into the body member 410 of the screw assembly 400 is shown. As shown in the figure, the distal end 104 of the driver shaft 100 has been engaged with the screw head 404 and as the main shaft 250 of the instrument 10 is pushed in a downward direction towards the screw assembly 400, the main shaft 250 and thus the jaw assembly 260 approaches the body member 410.

Figure 6:
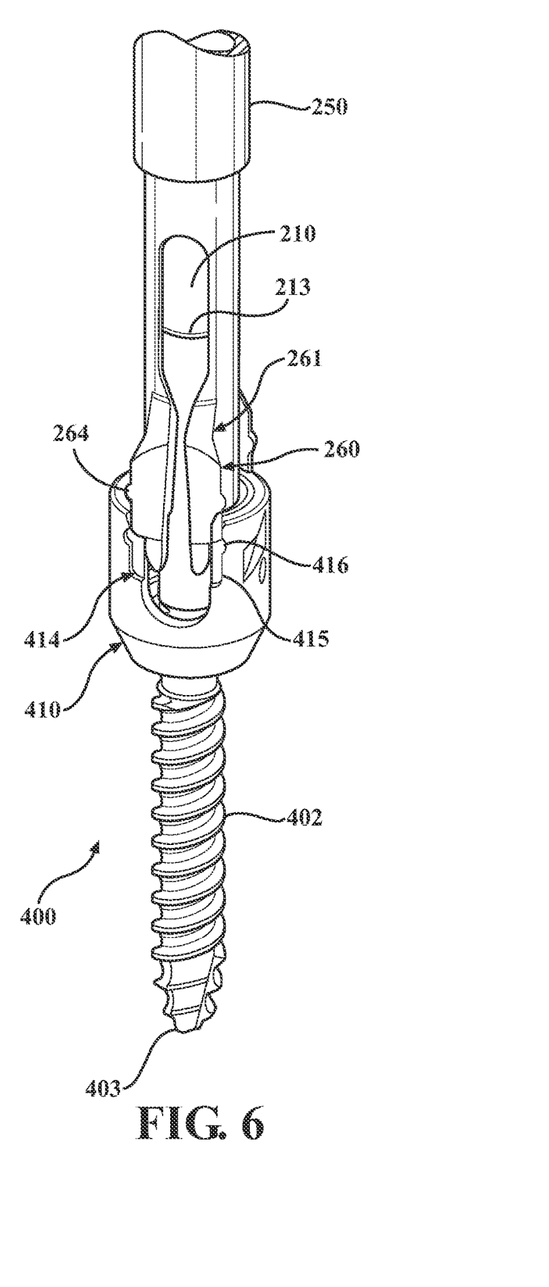
FIG. 6 is a perspective view of a distal end of the instrument shown in FIG. 1 while being attached to a screw assembly.
Figure 7:
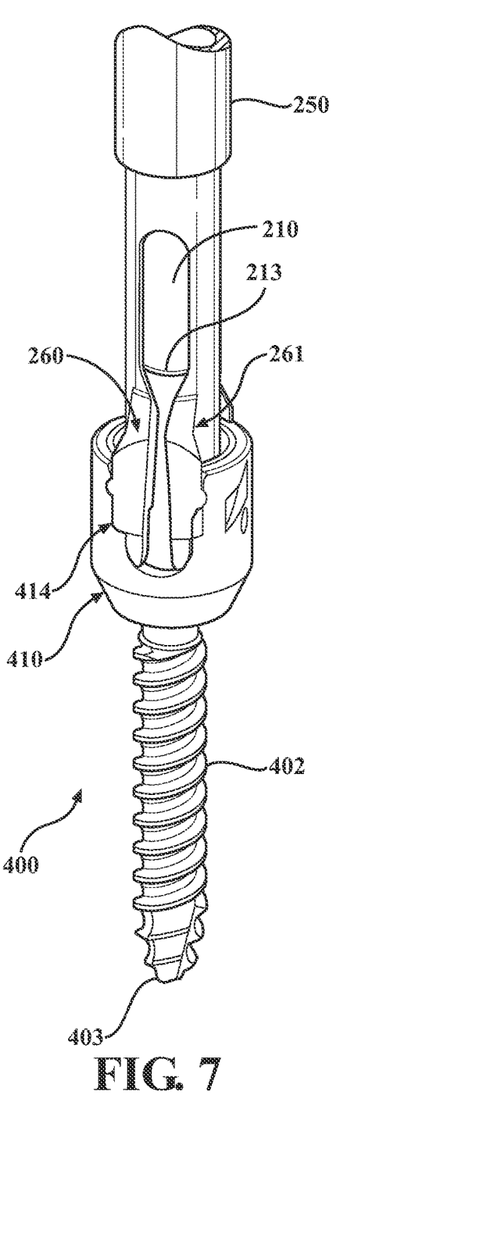
FIG. 7 is a perspective view of a distal end of the instrument shown in FIG. 1 after being attached to a screw assembly.

Further motion of the main shaft 250 in a direction towards the screw assembly 400 is shown in FIG. 6 in which the jaw assembly 260 is entering within the landings 414 of the body member 410. Finally, FIG. 7 illustrates the jaw assembly 260 fully inserted within the body member 410 such that the projections 264 of the jaw 261 are engaged with the indentations 416 of the landing 414. In addition, it is appreciated that the space or distance between opposing indentations 416 of the body member 410 are such that the pair of oppositely disposed jaws 261 are placed in a slight compressive state. Stated differently, the jaws 261 are lockably engaged with the body member 410 by a slight outer force of the jaws against the body member 410 and the landings 414.

Figure 8:
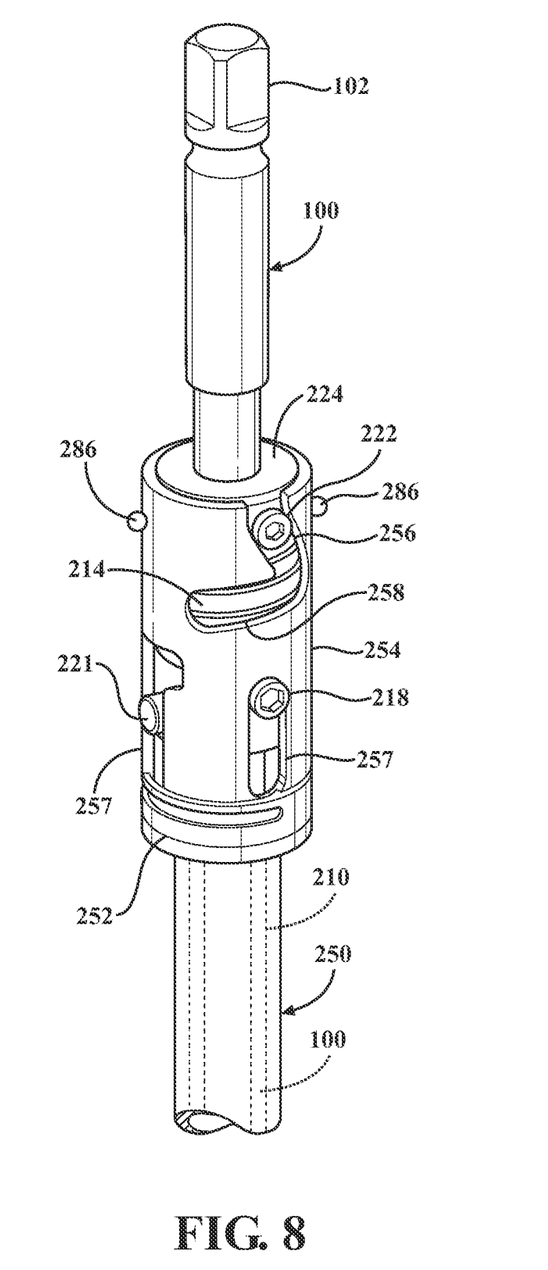
FIG. 8 is a perspective view of a main shaft, a main shaft housing, and a locking tube and driver shaft located within the main shaft.

Turning now to FIGS. 8-11, details of the housing 300 and its interworkings and mechanism during attachment of the jaw assembly 260 to the screw assembly 400 are shown and discussed. In particular, FIG. 8 provides a perspective view of the driver shaft 100, main shaft 250, and locking tube 210 without the presence of the housing cover 270. As shown in this figure, the driver shaft 100 is slidably mounted within the locking tube 210 and the locking tube 210 is slidably mounted within the main shaft 250. In addition, the housing 214 of the locking tube 210 is located or slidably mounted within the inner housing 254 of the main shaft 250. The locking tube housing 214 has the pair of cam screws 222 attached thereto via apertures 219, as well as the housing cover screw 218 and locking plates 220 with post 221.

It is appreciated from FIG. 8 that the locking tube housing 214 can slide within the inner housing 254 of the main shaft 250. In addition, the housing cover 270 with housing cover screw apertures 272 allow for the transmission of axial force on the housing cover 270 to be transmitted to the locking tube 210 via the housing cover screw 218.

Figure 9:
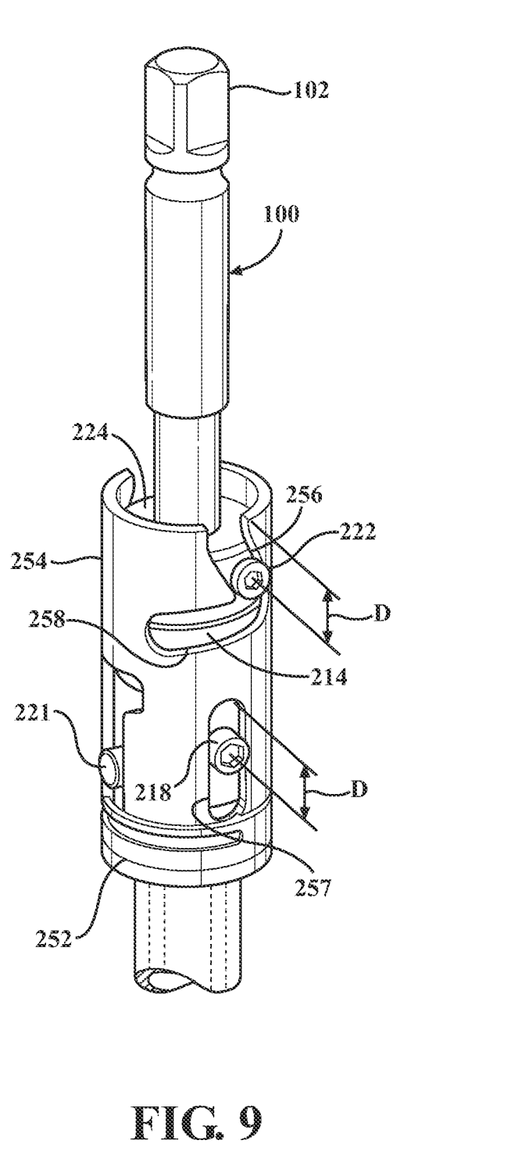
FIG. 9 is a perspective view of the embodiment shown in FIG. 8 with the locking tube in a different position relative to FIG. 8.

The cam raceway 256 and cam locking ramp 258 of the inner housing 254 provide an initial resistance against torsional load from the cam torsion spring 217 and prevent unnecessary axial motion of the locking tube 210 until the jaw assembly 260 is engaged with the screw assembly 400. Stated differently, the slope or angular path of the cam raceway 256 provides a resistance to the downward movement of the locking tube housing 214, and thus the locking tube 210, relative to the main shaft 250. However, once the jaw assembly 260 has been lockably engaged with the screw assembly 400 as shown in FIG. 7, increased axial force during the single action results in the cam screws 222 and thus the housing 214 to advance towards the screw assembly 400. As shown in FIG. 9, both the cam screw 222 and housing cover screw 218 move in a downward direction a distance 'D' which results in the distal end 213 of the locking tube 210 to move towards the screw assembly 400 and in between the pair of oppositely disposed jaws 261 of the jaw assembly 260 a distance 'D'. The movement down the raceway causes the cam torsion spring 217 to rotate and cause a torsional tensioning of the spring. This torsional load is stored by the spring and released at the bottom of the raceway when the cam screws enter the cam locking ramp 258 as described in more detail below.

Figure 10:
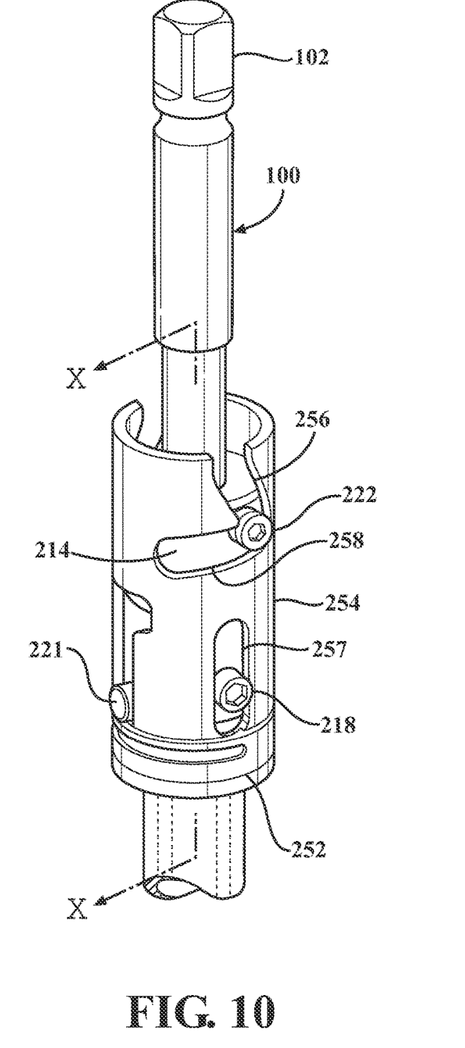
FIG. 10 is a perspective view of the housing shown in FIGS. 8 and 9, but at a different position.
Figure 11:
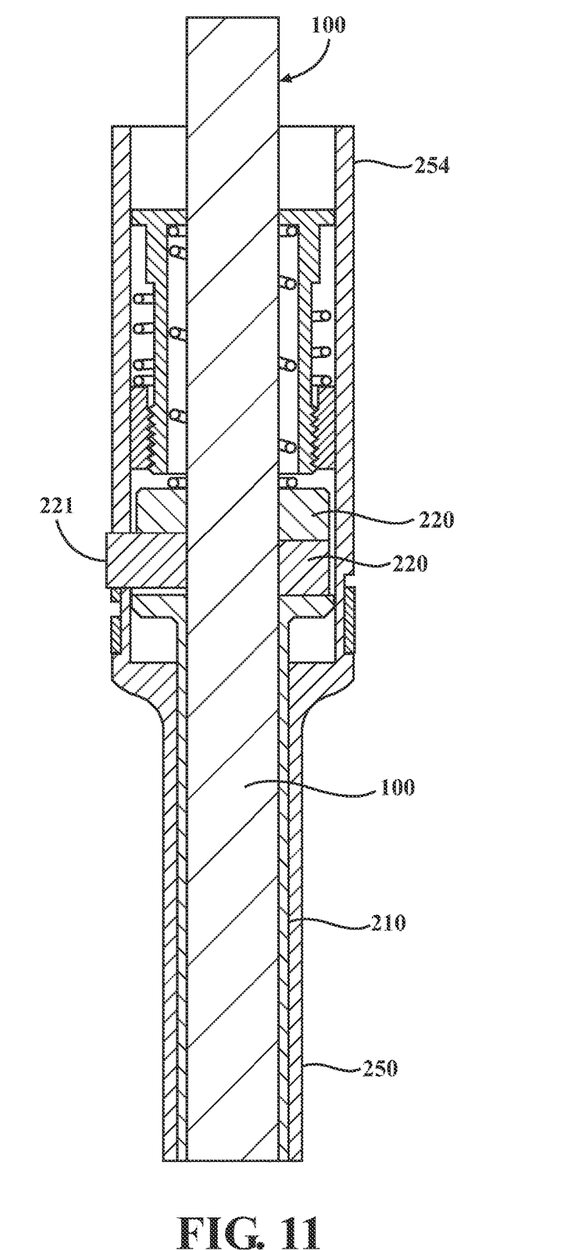
FIG. 11 is a side cross-sectional view of the housing shown in FIG. 10.

Just before the cam screws 222 reach the bottom of the raceway 256 the post 221 of the locking plates 220 contacts the locking plate spring clip 252 and affords for the locking plates 220 to tilt and bind against the driver shaft 100. In this bind or locked position, the driver shaft is held in a fixed position relative to the locking tube 210. Thus all further axial motion as the cam screws 222 round the bottom corner of the raceway 256 and moves down the bottom angled slot 258 causes the driver shaft 100 to preload the screw head 404 against the body member 410 and thus the screw to be rigidly locked to the driver. Once the cam screws 222 reach a bottom portion of the cam raceway 256 as shown in FIG. 10, downward movement of the housing cover 270 stops. Stated differently, contact between the locking plate post 221 and the locking plate spring clip 252 tilts the locking plates 220 and thus causes the center aperture 225 to catch or bind against the driver shaft 100 as illustrated in FIG. 11.

It is also at this location that the locking tube 210 and its distal end 213 are in a locked position. In particular, the locking tube 210 produces an outward force on the jaws 261 such that the projections 264 of each of the jaws 261 are engaged with the indentations 416 of the landing 414 that is part of the body member 410. It should be appreciated that at this position of the instrument 10 with respect to the screw assembly 400, the distal end 104 is within and engaged with the female screw head 404, however this is not required.

Figures 12, 13:
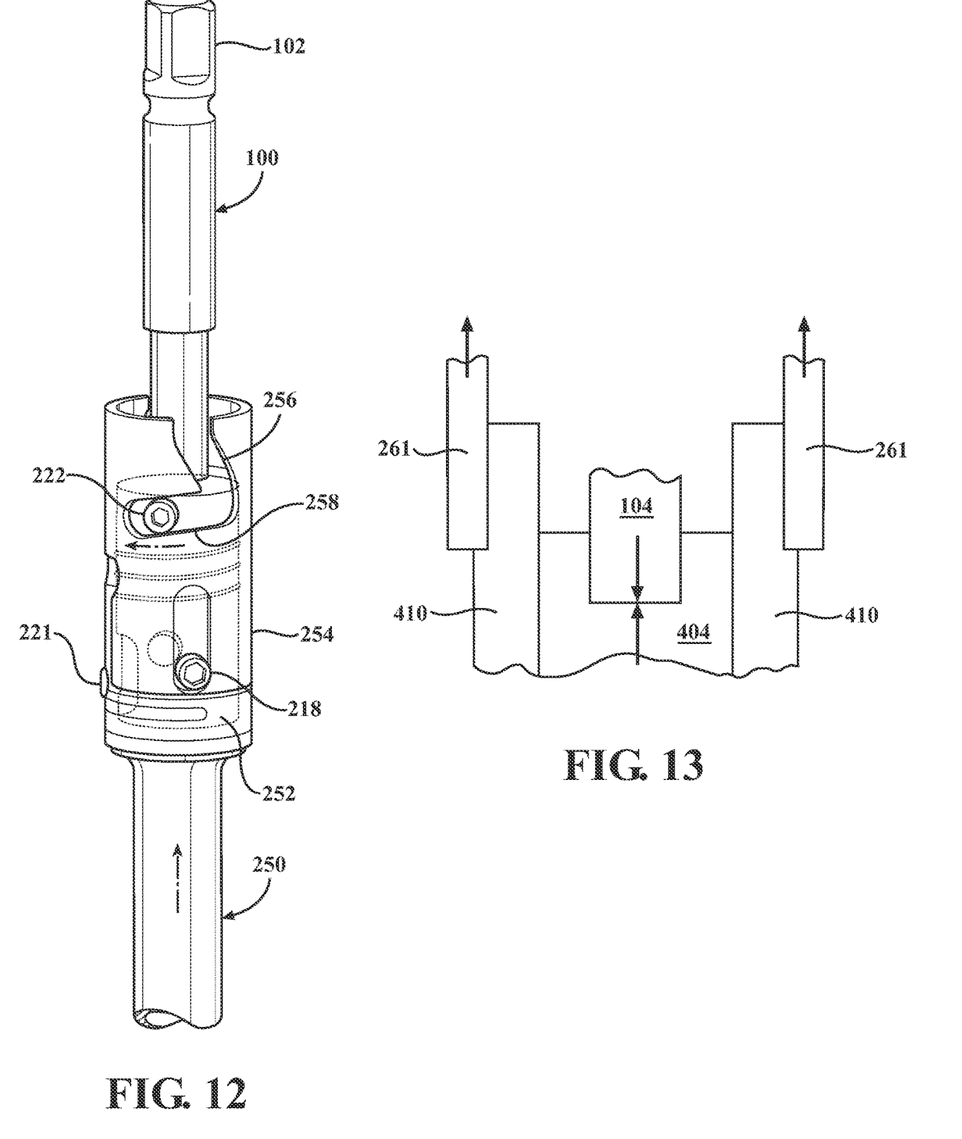
FIG. 12 is a perspective view of the housing shown in FIGS. 8, 9 and 10, but at a different position.
FIG. 13 is a side view of the distal end of the instrument attached to a screw assembly with a tension applied to a jaw assembly of the instrument.

Turning now to FIG. 12, an illustrative example of a preload mechanism 500 is provided. The preload mechanism 500 is configured to simultaneously urge the distal end 104 of the driver shaft 100 towards the screw head 404 and pull the body member 410 away from the distal end 104. For example, one embodiment of the preload mechanism is a jaw assembly tensioner 600 that pulls the pair of opposing jaws 261 attached to the body member 410 away from the distal end 104 of the driver shaft 100. In particular, the cam screws 222 located within the locking ramp 258 as illustrated in the figure provide for the locking tube 210 and driver shaft 100 to be locked together. Also, movement of the cam screws 222 down the cam locking ramp 258 causes the main shaft 250 and jaw assembly 260 to be pulled back against the distal end 104 of the driver shaft 100 and thereby cause the preload condition where the screw head 404 is driven against the body member 410. Thus, the jaw assembly tensioner 600 is configured to generate a preload condition within the screw head 404 by generating an opposing force between the jaw assembly 260 and the driver shaft 100.

In operation, with the locking tube 210 and driver shaft 100 locked together per the locking plates 220, movement of the cam screw 222 may be provided down and/or along the cam locking ramp 258. In particular, movement of the cam screw 222 along the cam locking tamp 258 affords for the main shaft 250 and jaw assembly 260 to be pulled back against the distal end 104 of the driver shaft 100. The movement of the cam screw 222 along the cam locking ramp 258 is provided by the cam torsion spring 217, and more so by turning or rotating of the release knob 280 such that the cam screw 222 is forced down the ramp 258. This pulling or tension of the main shaft 250 against the distal end 104 that is engaged with the female screw head 404 provides a preload condition where the screw head 404 is driven against or placed in compression with a ball socket of the body member 410. Furthermore, torsional load stored in the torsion spring 217 biases the cam screw 222 to advance down or along the cam locking ramp 258 such that a tightening or tensioning force that creates the preload condition is provided. FIG. 13 shows a schematic illustration of the preload condition with respect to the screw head 404, distal end 104 of the driver shaft 100, and the jaw assembly 260.

In this manner, the instrument 10 lockingly engages the screw assembly 400 and affords for the screw 402 to be driven or screwed into a bone portion of a patient. In addition, once the screw has been properly placed within the bone portion of the patient, the instrument 10 is released from the screw assembly 400 by turning of the release knob 280 such that the cam screw 222 travels up along the cam locking ramp 258 and further up the cam raceway 256. Upon this action, the locking plates untilt and release the driver shaft 100. Furthermore, the locking tube 210 moves in a direction away from the screw assembly 400 such that the outer force on the pair of oppositely disposed jaws 261 is no longer provided by the distal end 213. This then allows for the surgeon to pull upon the instrument 10 and the jaw assembly 260 to be removed from the body member 410. Naturally, the distal end 104 of the driver shaft 100 is also pulled away from the screw head 404.

The present invention improves upon the prior art by affording for a male tip 104 of the driver shaft 100 to engage a female socket 404 of the screw 402 while simultaneous sliding of the housing 300 down the driver shaft 100 ensures that the screw jaw assembly 260 engages the screw assembly 400 in a simple, secure and aligned manner. Stated differently, after the driver tip 104 is in place with respect to a female socket 404 of a screw assembly 400, the inventive instrument allows jaws 261 to engage and be attached to landings 414 that are machined proximate a slotted opening in the body member 410.

As the housing 300 of the instrument is moved down towards the screw assembly 400, the mating or complementary projection/indentation features 264 and 416 cause the jaws 261 to snap into place and positively engage the landings 414 on the screw body member 410. With the jaws 261 in place and securely attached to the body member 410, a continued sliding of the housing 300 moves an inner sleeve, e.g. the distal end 213 of the locking tube 210, between the pair of oppositely disposed jaws 261 and locks the jaws 261 into the screw assembly 400. The distal end 213 of the locking tube 210 interferes between the jaws 261 and the driver shaft 100 to prevent the jaws 261 from flexing radially inward. Furthermore, after the jaws 261 are locked to the screw assembly 400, the post 221 of the locking plates 220 affords tilting of the locking plates 220, such that the locking plates 220 bind against the driver shaft 100 and the shaft is locked into a fixed position relative to the housing 300. This combination of housing 300 movement towards the screw assembly 400, sliding of the locking tube distal end 213 between the jaws 261, and tilting of the locking plates 220 to bind the driver shaft 100 provides the locking mechanism 500 for the instrument 10.

In addition to the above, a timed cam action allows the cam screw 222 that is part of the locking tube housing 214 to slide down the cam locking ramp 258 and create the same preloaded condition and feel of the driver shaft 100 against the screw assembly 400 that exists when the sleeve is tightened in a standard screwdriver as discussed above. It is appreciated that the cam screw 222, cam locking ramp 258, etc., can also be part of the instrument locking mechanism 500, however this is not required. Stated differently, the instrument 10 can have a two-stage or two-part locking mechanism 500 in which the first-stage locks the jaws 261 to the screw assembly 400 via the locking tube 210 and locks the driver shaft 100 via the locking plates 220. Also, the second stage removes any slack between the driver shaft distal end 104 and the screw head 404 via the cam screw 222 and cam locking ramp 258. In the alternative, the instrument 10 can be considered to have a one-stage locking mechanism 500 that locks the jaws 261 and the driver shaft 100, and a separate tensioning mechanism. However, it is appreciated the locking mechanism 500 and jaw assembly tensioner 600 provided herein are illustrative and the locking mechanism and jaw assembly tensioner 600 for use in the instrument 10 provided herein are actuated with the single action/stabbing motion. In this manner, a driver, e.g. a pedicle screwdriver, can be easily coupled to a screw assembly using a simple single action/one-push motion of the driver. The action or motion may thus be performed in a single direction commonly used to thrust a screwdriver into frictional/compressive engagement of the driver tip within the screw head. Currently, such single direction action is used to temporarily hold the screw assembly 400 to the driver tip until the surgeon performs additional acts to further retain the instrument to the screw assembly.

The instrument also provides a rigid connection with the screw as a result of the one-push motion and thus affords for a tactile feedback to a surgeon as the screw is advanced into a bone of a patient. The applied tension aligns the screw and body member axially with the instrument. It is appreciated that the feedback is generated by friction between the bone and a surface of the screw which can generate subtle vibrations that can only be transmitted through a rigid preloaded connection between the driver and the screw. As noted above, such a rigid preload is accomplished in prior art instruments by threading a sleeve of the instrument into the screw body. However, the preload of the inventive instrument is accomplished by locking the housing 300 to the driver shaft just as a cam screw/pin enters a ramp with a slope that is approximately equal to a pitch of the threaded sleeve. Furthermore, a torsion spring that is rotated to generate a torsion load drives the cam screw/pin down the ramp to produce a tightening force that preloads the screw and the screw body assembly.

It is appreciated that changes and modifications to the embodiments disclosed herein will be apparent to one skilled in the art and yet fall within the scope of the present invention. Therefore, such changes, modifications, and the like are part of the invention and the specification and the following claims, both of which provide the scope of the invention, should be interpreted broadly.

We claim:

1. An instrument for attachment to a screw assembly using a single action motion, said instrument further configured to insert a screw into a surgical site, said instrument comprising:
   a main shaft having a distal end, a locking tube, and a driver shaft, said locking tube slidably mounted within said main shaft and said driver shaft slidably mounted within said locking tube; and
   a locking mechanism comprising a locking plate with an aperture, said locking plate attached to said locking tube and said driver shaft extending through said aperture and completely encircled by said locking plate, said locking mechanism configured to lock said driver shaft in a fixed position in relation to said locking tube by translating a distal movement of one of said main shaft or said locking tube with respect to said driver shaft.

2. The instrument of claim 1, wherein said locking plate has a tilt position, said locking plate binding said driver shaft in said fixed position when in said tilt position.

3. The instrument of claim 2, wherein said distal end of said main shaft has a pair of opposing jaws having a contoured edge dimensioned to engage a body member of the screw assembly.

4. The instrument of claim 3, wherein said locking tube slides between said pair of opposing jaws during translating the distal movement of one of said main shaft or said locking tube with respect to said driver shaft.

5. The instrument of claim 4, wherein said locking tube slid between said pair of opposing jaws locks said pair of opposing jaws to the body member of the screw assembly.

6. The instrument of claim 1, further comprising a preload mechanism configured to urge a distal end of said driver shaft towards a screw head of the screw assembly and pull a body member of the screw assembly away from said distal end of said driver shaft.

7. The instrument of claim 6, wherein said preload mechanism is a jaw assembly tensioner configured to pull a pair of opposing jaws attached to the body member of the screw assembly away from said distal end of said driver shaft.

8. The instrument of claim 7, wherein said jaw assembly tensioner has a cam screw attached to said locking tube and a locking ramp within said main shaft, said cam screw moving along said locking ramp configured to pull said pair of opposing jaws away from a distal end of said driver shaft after said locking tube locks said pair of opposing jaws to the body member of the screw assembly.

9. The instrument of claim 8, further comprising a housing coupled to said main shaft and dimensioned to be grasped by a surgeon and assist in the single action motion.

10. A screw assembly and an instrument for attachment to the screw assembly using a single action motion, comprising:
   a screw with a body member mounted onto said screw, the body member having a slot with an outer contoured edge;
   a housing;
   a main shaft having a proximal end coupled to said housing and a distal end with a screw jaw assembly, said screw jaw assembly having a pair of opposing jaws, each of said pair of opposing jaws having an outer contoured edge that is complementary with said outer edge of said slot;
   a locking tube slidably disposed within said main shaft and having a proximal end coupled to said housing and a distal end configured to engage said screw jaw assembly by sliding between said pair of opposing jaws and exerting an outward force therebetween, said outward force between said pair of opposing jaws engaging said outer contoured edge of each of said pair of opposing jaws with said outer contoured edge of said slot and attaching said pair of opposing jaws to the screw assembly; and
   a drive shaft slidably disposed within said locking tube and having a distal end configured to engage the screw head of the screw assembly.

11. The screw assembly and instrument of claim 10, wherein said outer contoured edge of said slot of said body member has an indentation.

12. The screw assembly and instrument of claim 11, wherein said outer contoured edge of each of said pair of opposing jaws has a projection that is complementary in shape with said indentation of said outer contoured edge of said slot of said body member.

13. The screw assembly and instrument of claim 10, further comprising a locking mechanism configured to lock said driver shaft in a fixed position relative to said locking tube, said locking mechanism selected from the group consisting of a locking plate that binds against said driver shaft, a spring loaded detent, and a pin and groove catch.

14. The screw assembly and instrument of claim 13, wherein said locking mechanism is said locking plate with a tilt position and an un-tilt position, said locking plate having an aperture and said driver shaft extending through said aperture.

15. The screw assembly and instrument of claim 14, wherein said locking plate in said tilt position binds an edge of said aperture against said driver shaft and locks said driver shaft in said fixed position relative to said locking tube.

16. The screw assembly and instrument of claim 15, wherein said locking plate is a pair of locking plates, each of said pair of locking plates having an aperture with said driver shaft extending therethrough, each of said pair of locking plates also have said tilt position and said un-tilt position.

17. The screw assembly and instrument of claim 10, further comprising a preload mechanism configured to urge a distal end of said driver shaft towards the screw head of the screw assembly and pull a body member of the screw assembly away from said distal end of said driver shaft.

18. The screw assembly and instrument of claim 17, wherein said preload mechanism is a jaw assembly tensioner configured to pull a pair of opposing jaws attached to the body member of the screw assembly away from said distal end of said driver shaft.

19. The screw assembly and instrument of claim 18, wherein said jaw assembly tensioner has a cam screw attached to said locking tube and a locking ramp within said main shaft, said cam screw moving along said locking ramp configured to pull said pair of opposing jaws away from a distal end of said driver shaft after said locking tube locks said pair of opposing jaws to the body member of the screw assembly.

* * * * *